US00PP28365P3

(12) United States Plant Patent
Verwer

(10) Patent No.: US PP28,365 P3
(45) Date of Patent: Sep. 5, 2017

(54) ***DAHLIA* PLANT NAMED 'DAHLGR85'**

(50) Latin Name: *Dahlia hybrida*
Varietal Denomination: Dahlgr85

(71) Applicant: Aad W. M. Verwer, Lisse (NL)

(72) Inventor: Aad W. M. Verwer, Lisse (NL)

(73) Assignee: Verwer Dahlias B.V., Lisse (NL)

( * ) Notice: Subject to any disclaimer, the term of this patent is extended or adjusted under 35 U.S.C. 154(b) by 14 days.

(21) Appl. No.: 14/998,434

(22) Filed: Dec. 31, 2015

(65) Prior Publication Data

US 2017/0196154 P1 Jul. 6, 2017

(51) Int. Cl.
*A01H 5/02* (2006.01)

(52) U.S. Cl.
USPC ..... Plt./321

(58) Field of Classification Search
USPC ..... Plt./321
See application file for complete search history.

*Primary Examiner* — Susan McCormick Ewoldt
(74) *Attorney, Agent, or Firm* — C. A. Whealy

(57) ABSTRACT

A new and distinct cultivar of *Dahlia* plant named 'Dahlgr85', characterized by its relatively compact, mounding and dense plant habit; freely basal branching habit; dark green-colored leaves; early and freely flowering habit; single-type inflorescence form; large inflorescences with dark pink and red bi-colored ray florets; and good postproduction longevity and garden performance.

2 Drawing Sheets

Botanical designation: *Dahlia hybrida.*
Cultivar denomination: 'DAHLGR85'.

BACKGROUND OF THE INVENTION

The present invention relates to a new and distinct cultivar of *Dahlia* plant, botanically known as *Dahlia hybrida*, and hereinafter referred to by the name 'Dahlgr85'.

The new *Dahlia* plant is a product of a planned breeding program conducted by the Inventor in Lisse, The Netherlands. The objective of the breeding program is to create new compact container and garden *Dahlia* plants with dark-colored leaves, large inflorescences and good postproduction longevity.

The new *Dahlia* plant originated from a cross-pollination conducted by the Inventor during the summer of 2010 of a proprietary seedling selection of *Dahlia hybrida* identified as code number VD5-127, not patented, as the female, or seed, parent with a proprietary seedling selection of *Dahlia hybrida* identified as code number VD5-272, not patented, as the male, or pollen, parent. The new *Dahlia* plant was discovered and selected by the Inventor as a single flowering plant from within the progeny of the stated cross-pollination in a controlled greenhouse environment in Lisse, The Netherlands during the summer of 2011.

Asexual reproduction of the new *Dahlia* plant by cuttings since February, 2012 in a controlled greenhouse environment in Lisse, The Netherlands, has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Dahlgr85'. These characteristics in combination distinguish 'Dahlgr85' as a new and distinct *Dahlia* plant:

1. Relatively compact, mounding and dense plant habit.
2. Freely basal branching habit.
3. Dark green-colored leaves.
4. Early and freely flowering habit.
5. Single-type inflorescence form.
6. Large inflorescences with dark pink and red bi-colored ray florets.
7. Good postproduction longevity and garden performance.

Plants of the new *Dahlia* differ primarily from plants of the female parent selection in the following characteristics:

1. Plants of the new *Dahlia* are more compact than plants of the female parent selection.
2. Plants of the new *Dahlia* and the female parent selection differ in leaf color as plants of the female parent selection have bronze-colored leaves.
3. Plants of the new *Dahlia* and the female parent selection differ in ray floret color as plants of the female parent selection have red and yellow bi-colored ray florets.

Plants of the new *Dahlia* differ primarily from plants of the male parent selection in the following characteristics:

1. Plants of the new *Dahlia* are taller than plants of the male parent selection.
2. Plants of the new *Dahlia* and the male parent selection differ in leaf color as plants of the male parent selection have bronze-colored leaves.
3. Plants of the new *Dahlia* and the male parent selection differ in ray floret color as plants of the male parent selection have brownish red and golden yellow bi-colored ray florets.

Plants of the new *Dahlia* can be compared to plants of the *Dahlia hybrida* 'HS Wink', disclosed in U.S. Plant Pat. No. 18,424. In side-by-side comparisons conducted in Lisse, The Netherlands, plants of the new *Dahlia* differed from plants of 'HS Wink' in the following characteristics:

1. Plants of the new *Dahlia* were more compact than plants of 'HS Wink'.
2. Plants of the new *Dahlia* flowered about five days later than plants of 'HS Wink'.
3. Plants of the new *Dahlia* had larger inflorescences than plants of 'HS Wink'.
4. Plants of the new *Dahlia* and 'HS Wink' differed in ray floret color as plants of 'HS Wink' had light purple and red purple bi-colored ray florets.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet comprises a side perspective view of a typical flowering plant of 'Dahlgr85' grown in an outdoor nursery.

The photograph on the second sheet is a close-up view of a typical flowering plant of 'Dahlgr85'.

DETAILED BOTANICAL DESCRIPTION

The photographs and following observations and measurements describe plants grown during the late summer and early autumn in ground beds in an outdoor nursery in Lisse, The Netherlands and under cultural practices typical of commercial *Dahlia* production. During the production of the plants, day temperatures ranged from 15° C. to 30° C. and night temperatures ranged from 10° C. to 20° C. Plants were pinched one time about four weeks after planting. Plants were three months old when the photographs were taken and four months old when the description was taken. In the following description, color references are made to The Royal Horticultural Society Colour Chart, 1995 Edition, except where general terms of ordinary dictionary significance are used.

Botanical classification: *Dahlia hybrida* 'Dahlgr85'.

Parentage:

*Female, or seed, parent*.—Proprietary seedling selection of *Dahlia hybrida* identified as code number VD5-127, not patented.

*Male, or pollen, parent*.—Proprietary seedling selection of *Dahlia hybrida* identified as code number VD5-272, not patented.

Propagation:

*Type*.—By vegetative cuttings.

*Time to initiate roots, summer*.—About twelve days at soil temperatures about 15° C. and air temperatures ranging from about 15° C. to 25° C.

*Time to initiate roots, winter*.—About 13 to 14 days at soil temperatures about 15° C. and air temperatures ranging from about 15° C. to 25° C.

*Time to produce a rooted young plant, summer*.—About 20 days at soil temperatures about 15° C. and air temperatures ranging from about 15° C. to 25° C.

*Time to produce a rooted young plant, winter*.—About 21 days at soil temperatures about 15° C. and air temperatures ranging from about 15° C. to 25° C.

*Root description*.—Fine, fleshy.

*Rooting habit*.—Moderately freely branching; dense.

*Tubers*.—Length: About 19 cm. Diameter: About 21 cm. Texture: Corky. Color: Close to 164D.

Plant description:

*Plant and growth habit*.—Relatively compact and mounding plant habit; appropriate for 18-cm to 25-cm containers; inverted triangular plant form; freely basal branching with about six primary lateral branches developing per plant; dense and bushy appearance; inflorescences held above the foliar plane on strong peduncles; vigorous growth habit.

*Plant height*.—About 55 cm.

*Plant diameter or spread*.—About 35 cm.

*Lateral branches*.—Length: About 45 cm. Diameter: About 2 cm. Internode length: About 5 cm to 18 cm. Texture: Smooth, glabrous. Strength: Strong. Aspect: Erect to about 20° from vertical. Color: Close to 146B; towards the apex, heavily tinged with close to 166A.

Leaf description:

*Arrangement*.—Opposite, simple or compound with three or five leaflets per leaf.

*Leaf length, simple leaves*.—About 8 cm.

*Leaf width, simple leaves*.—About 5 cm.

*Leaf length, compound leaves with three leaflets*.—About 13 cm.

*Leaf width, compound leaves with three leaflets*.—About 10 cm.

*Leaf length, compound leaves with five leaflets*.—About 22 cm.

*Leaf width, compound leaves with five leaflets*.—About 12 cm.

*Shape, simple leaves or leaflets*.—Ovate.

*Apex, simple leaves or leaflets*.—Acuminate.

*Base, simple leaves or leaflets*.—Attenuate.

*Margin, simple leaves or leaflets*.—Slightly serrate; sinuses divergent.

*Venation pattern, simple leaves or leaflets*.—Pinnate, reticulate.

*Texture, upper and lower surfaces, simple leaves or leaflets*.—Smooth, glabrous.

*Color*.—Developing leaves or leaflets, upper surface: Darker than 200A. Developing leaves or leaflets, lower surface: Close to 148A. Fully expanded leaves or leaflets, upper surface: Darker than 147A; venation, close to 59A. Fully expanded leaves or leaflets, lower surface: Close to 147B; venation, close to 187A.

*Petioles*.—Length, simple leaves: About 9 mm. Length, compound leaves with three leaflets: About 3 cm. Length, compound leaves with five leaflets: About 7 cm. Diameter, simple leaves or leaflets: About 2.5 mm. Texture, upper and lower surfaces, simple leaves or leaflets: Smooth, glabrous. Color, simple leaves or leaflets, upper surface: Close to 146D. Color, simple leaves or leaflets, lower surface: Close to 146C tinged with close to 187C.

Inflorescence description:

*Appearance and flowering habit*.—Single-type inflorescences with ray and disc florets developing acropetally on a receptacle; inflorescences positioned above and beyond the foliar plane on strong peduncles; inflorescences face upright to outwardly; freely flowering habit with typically about 60 inflorescences developing per plant during the flowering season.

*Fragrance*.—None detected.

*Time to flower*.—Early flowering habit; plants begin flowering about 65 days after planting; flowering continuous during the summer and autumn in The Netherlands.

*Post-production longevity*.—Good postproduction longevity; inflorescences maintain good substance for about twelve days on the plant and for about four to five days as a cut flower; inflorescences persistent.

*Inflorescence buds*.—Height: About 1.6 cm. Diameter: About 2.1 cm. Shape: Oblate. Texture: Smooth, glabrous. Color: Close to 147A tinged with close to 59B.

*Inflorescence diameter*.—Large, about 9.8 cm.

*Inflorescence depth* (*height*).—About 2.6 cm.

*Disc diameter*.—About 2.6 cm.

*Receptacle height*.—About 1 cm.

*Receptacle diameter*.—About 1.8 cm.

*Ray florets*.—Number of ray florets per inflorescence: About eight arranged in a single whorl. Length: About 4.7 cm. Width: About 3.1 cm. Shape: Ovate. Apex: Obtuse. Base: Attenuate. Margin: Entire. Aspect: Initially upright to roughly perpendicular to the peduncle. Texture and luster, upper and lower surfaces: Smooth, glabrous; velvety to shiny. Color: When opening and fully opened, upper surface: Towards the base, close to 46A; mid-section, close to 24D; towards the apex, close to 67A; color does not change with development. When opening and fully opened, lower surface: Close to 70B; at the base, close to 11B; margins, close to 33B and 67B.

*Disc florets*.—Number of disc florets per inflorescence: About 130. Length: About 1.4 cm. Diameter: At the apex, about 2.1 mm; at the base, about 1.5 mm. Shape: Tubular; apex dentate, pentafid. Aspect: Mostly upright. Texture: Smooth, glabrous. Color, immature: Close to 187A. Color, mature: Apex: Close to 187A. Mid-section: Close to 178B. Base: Close to 1C.

*Phyllaries*.—Quantity per inflorescence: About five arranged in a single whorl. Length: About 1.6 cm. Width: About 1 cm. Shape: Ovate. Apex: Acuminate. Base: Attenuate. Margin: Entire. Texture, upper and lower surfaces: Smooth, glabrous. Color, upper surface: Close to 200A. Color, lower surface: Close to 200A; at the base, close to 146A.

*Peduncles*.—Length, terminal peduncle: About 19 cm. Length, fourth peduncle: About 17 cm. Length, seventh peduncle: About 11 cm. Diameter: About 4 mm. Strength: Strong. Aspect: Mostly erect to 20° from vertical. Texture: Smooth, glabrous. Color: Close to 187A.

*Reproductive organs*.—Androecium, present on disc florets only: Quantity per disc floret: Five. Anther length: About 1.2 cm. Anther shape: Lanceolate. Anther color: Close to 150D. Pollen amount: Moderate. Pollen color: Close to 23A. Gynoecium, present on ray and disc florets: Quantity per floret: One. Pistil length: About 7 mm. Stigma shape: Lanceolate. Stigma color: Close to 16B. Style length: About 2.8 mm. Style color: Close to 1B. Ovary color: Close to 150D. Seeds: Length: About 7 mm. Diameter: About 3 mm. Color: Close to 200C.

Disease & pest resistance: Plants of the new *Dahlia* have not been shown to be resistant to pathogens and pests common to *Dahlia* plants.

Garden performance: Plants of the new *Dahlia* have exhibited good tolerance to rain and wind and have been observed to tolerate temperatures from about 0° C. to about 35° C.

It is claimed:

1. A new and distinct *Dahlia* plant named 'Dahlgr85' as illustrated and described.

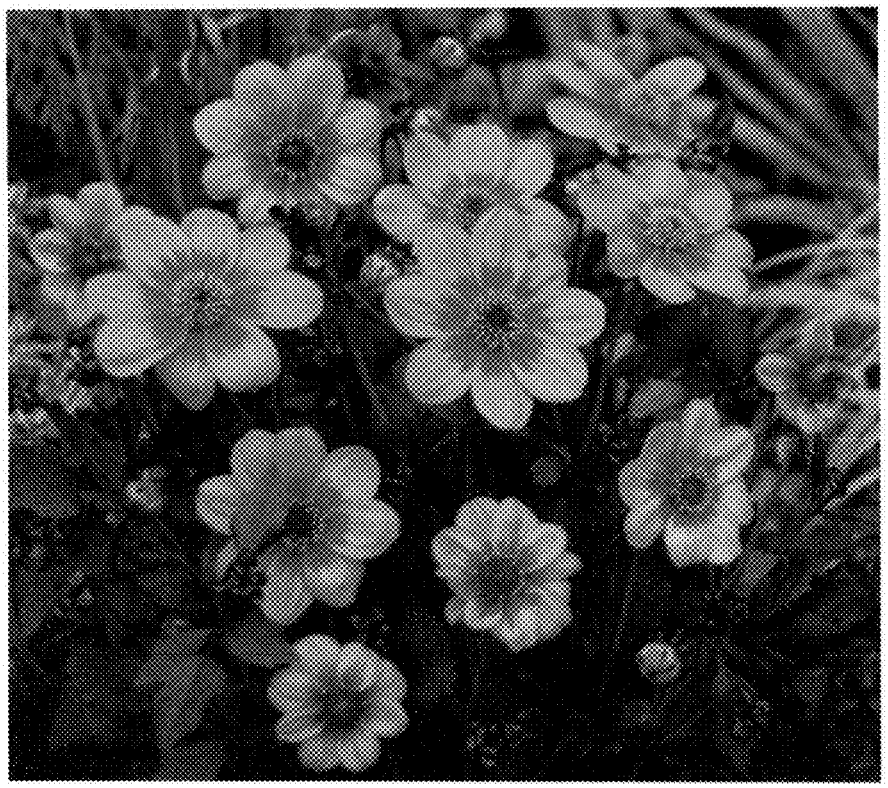

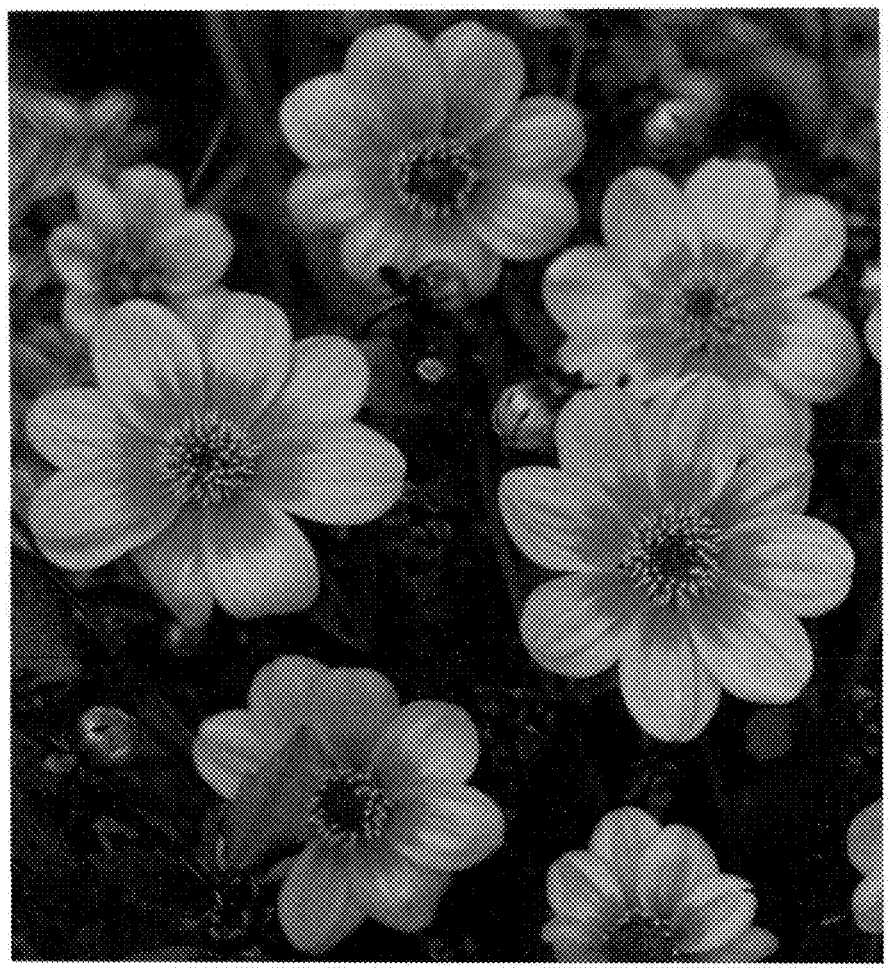

* * * * *